United States Patent [19]

D'Silva

[11] 4,072,751

[45] Feb. 7, 1978

[54] PESTICIDAL N-SUBSTITUTED BIS-CARBAMOYL SULFIDE COMPOUNDS

[75] Inventor: Themistocles Damasceno Joaquim D'Silva, South Charleston, W. Va.

[73] Assignee: Union Carbide Corporation, New York, N.Y.

[21] Appl. No.: 727,987

[22] Filed: Sept. 29, 1976

[51] Int. Cl.$^2$ .................. A01N 9/00; C07C 119/18
[52] U.S. Cl. .................. 424/298; 260/453 RW; 260/545 R; 260/551 R; 260/543 F; 424/320; 424/315

[58] Field of Search ............... 260/453 RW, 545, 551, 260/543 F; 424/298, 320

[56] References Cited

U.S. PATENT DOCUMENTS

| | | | |
|---|---|---|---|
| 3,726,908 | 4/1973 | Buchanan | 260/453 R |
| 3,856,972 | 12/1974 | Fujimoto et al. | 424/298 |

*Primary Examiner*—Leonard Schenkman
*Attorney, Agent, or Firm*—Richard C. Stewart

[57] ABSTRACT

N-Substituted bis-carbamoyl sulfide compounds exhibit pesticidal activity.

21 Claims, No Drawings

PESTICIDAL N-SUBSTITUTED BIS-CARBAMOYL SULFIDE COMPOUNDS

This invention relates to novel N-substituted bis-carbamoyl sulfide compounds and to their preparation. This invention is also directed to insecticidal, miticidal and nematocidal compositions comprising an acceptable carrier and an insecticidally, miticidally or nematocidally effective amount of a compound of this invention as well as to a method of controlling insects, mites and nematodes by subjecting them to an insecticidally, nematocidally or miticidally effective amount of a compound according to this invention. In another limited aspect this invention relates to a limited group of compounds, that in addition to their pesticidal activity are also useful intermediates in the preparation of other pesticidally active compounds.

More particularly, this invention relates to compounds of the formula:

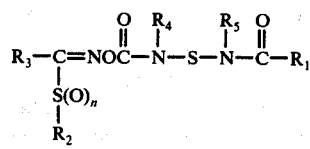

wherein:
$n$ is 1 or 2;
$R_1$ is fluorine or

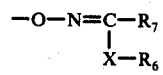

X is sulfur, sulfinyl or sulfonyl;
$R_2$, $R_3$, $R_4$, $R_5$, $R_6$ and $R_7$ are individually alkyl.

The compounds of this invention exhibit outstanding insecticidal, miticidal and nematocidal activity. The compounds of this invention are also characterized by substantially reduced mammalian toxicity and phytotoxicity in comparison with known pesticidally active compounds having a comparable spectrum of insecticidal, miticidal and nematocidal activity.

In general $R_2$, $R_3$, $R_4$, $R_5$, $R_6$ and $R_7$ substituents individually may not include more than eight carbon atoms. Preferred because of their higher level of pesticidal activity are the compounds of this invention in which $R_2$, $R_3$, $R_4$, $R_5$, $R_6$ and $R_7$ substituent individually include from 1 to 5 carbon atoms. Particularly preferred compounds are those wherein $R_3$, $R_4$, $R_5$ and $R_7$ are methyl. Other preferred compounds according to this invention are those in which $R_1$ is fluorine, due to their additional utility as intermediates in the preparation of pesticidally active compounds by reaction with oxime compounds, hydroxylated aryl compounds or other active hydrogen containing compounds. For example, 1-methylsulfinylacetaldehyde O-[N-methyl-N-(N'-methyl-N'-fluoroformylaminosulfenyl)carbamoyl] oxime may be reacted 2,2-dimethyl-2, 3-dihydro-7-hydroxybenzofuran in the presence of triethylamine as an acid acceptor to yield N-[1-methylsulfinylacetaldehyde-O-(N'-methylcarbamoyl)oxime]-N-[2, 2-dimethyl-2, 3-dihydro-7-(N-methylcarbamoyloxy)benzofuran] sulfide the corresponding pesticidally active carbamate compound.

The compounds of this invention can be prepared in accordance with a variety of methods. One preferred method for preparing compounds in which $R_1$ is fluorine is illustrated by the general reaction scheme set forth below in which $n$, $R_2$, $R_3$, $R_4$ and $R_5$ are as described above:

METHOD I

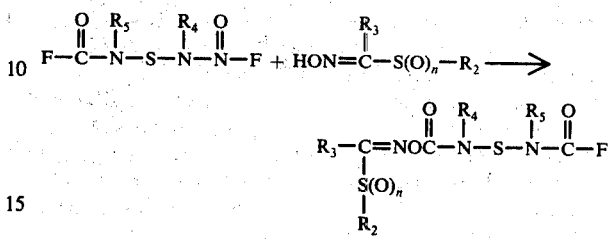

The compounds of this invention in which $R_1$ is other than fluorine can be prepared by reacting the reaction product of Method I, usually in situ, with an appropriately substituted oxime compound as illustrated in the reaction scheme set forth below in which $n$, $R_2$, $R_3$, $R_4$, $R_5$, $R_6$ and $R_7$ are as described above:

METHOD II

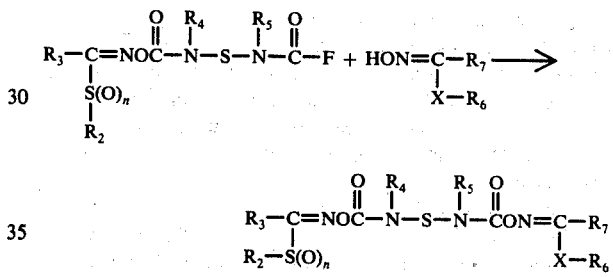

An alternative method of preparing compounds of this invention in which $R_3=R_7$, $R_2=R_6$ and $X=S(O)_n$ is illustrated by the general reaction scheme set forth below in which $R_2$, $R_3$, $R_4$, $R_5$ and $n$ are as described above:

METHOD III

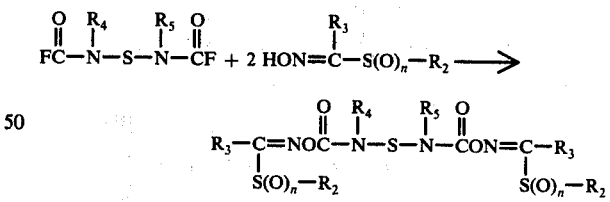

The reactions of Methods I and II are carried out by bringing together substantially equivalent amounts of the reactants in an inert solvent. In the reaction illustrated in Method III, two equivalents of the oxime reactant is reacted with one equivalent of the bis-carbamoyl flouride reactant in an inert solvent. Illustrative of inert solvent that are useful in the conduct of these reactions are benzene, toluene, methylene chloride, xylene, dioxane, tetrahydrofuran or the like.

Reaction temperatures are not critical and can be varied over a wide range depending to a large extent on the reactivity and the thermal stability of the reactants. Preferred reaction temperatures are from about −30° to about 100° C.

Reaction pressures are not critical. For convenience the reaction is usually conducted at atmospheric or autogeneous pressure.

These reactions are conducted in the presence of an acid acceptor. The molar ratio of the acid acceptor is usually equivalent to that of the oxime compound present in the reaction mixture although a slight excess of the acid acceptor may be used if desired. The acid acceptor may be either an organic or an inorganic base. Illustrative of organic bases that are useful as acid acceptors are tertiary amines, alkali metal alkoxides or the like. Bases such as sodium hydroxide, potassium hydroxide or the like are illustrative of inorganic bases that are useful. Preferred organic acid acceptors are tertiary amines such as triethylamine, pyridine, trimethylamine, 1, 4-diazobicyclo [2.2.2] octane or the like.

These reactions can be conducted in a homogeneous (mono) phase system, or when an inorganic base is employed as the acid acceptor, in a heterogeneous phase system. In the latter case phase transfer agents such as crown ether compounds, quaternary ammonium halide compounds or the like may be used to facilitate the transfer of the reactants across the phase interface. For example, when a solid inorganic base is employed as an acid acceptor in an organic solvent medium a crown ether compound may be used as a phase transfer agent, or alternatively when these reactions are conducted in a two-solvent phase system, which consists of an aqueous solution of an inorganic base acid acceptor as one phase and an organic solvent containing dissolved reactants as the other phase, a quaternary ammonium halide compound may be employed as the phase transfer agent.

Compounds of this invention in which $n$ is 1 or 2 and/or X is either a sulfinyl or a sulfonyl group can be prepared by the reaction illustrated in Methods I, II, and III. An alternative method of preparing compounds in which $X=S(O)_n$ is by selectively oxidising the bis-alkylthio compound with an oxidising agent, as for example peracetic acid or other organic peracids as illustrated in the following reaction scheme in which $n$, $R_2$, $R_3$, $R_4$, $R_5$, $R_6$ and $R_7$ are as described above:

METHOD IV

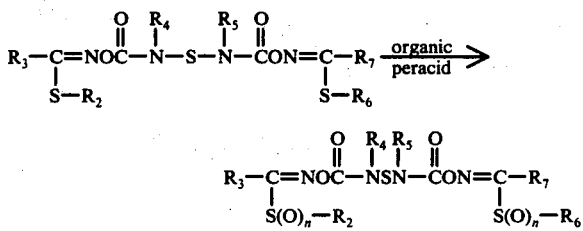

Oxime compounds utilized as reactants in the preparation of the compounds of this invention can be prepared according to a variety of methods. For example, 1-methylthioacetaldoxime can be prepared by reacting acetaldehyde with hydroxylamine hydrochloride to form acetaldoxime which is then treated with chlorine in hydrochloric acid solvent to form 1-chloroacetaldoxime which is then further reacted with sodium methylmercaptide to form the desired aldoxime compound. 1-Methylthioaldoxime is readily converted to the 1-methylsulfinyl and 1-methylsulfonyl derivatives by oxidation with peracetic acid. The above disclosed method together with other methods for preparing oxime compounds are described in more detail in U.S. Pat. Nos. 3,752,841; 3,726,908; 3,843,669; and Belgian Pat. No. 813,206 and 815,513.

Bis-(N-Alkyl-N-fluorocarbonylamino)sulfide compounds used as reactants in the preparation of the compounds of this invention can be conveniently prepared by a variety of methods. One preferred method consists of reacting hydrogen fluoride with an appropriately substituted alkylisocyanate compound to form the corresponding alkylaminocarbonylfluoride compound which is then reacted with sulfur dichloride (SCl$_2$) in the presence of at least two equivalents of an acid acceptor as described above, preferably in an inert solvent, to yield bis-(N-alkyl-N-fluorocarbonylamino)sulfide compound.

The following specific examples are presented to more particularly illustrate the manner in which the compounds of this invention can be prepared.

EXAMPLE I

Preparation of N', N'-bis-(N-methyl-N-fluorocarbonylamino)sulfide

To a polypropylene reactor containing 80 g (4.0 m) of hydrogen fluoride in 1800 ml of toluene, cooled to −40° C was added dropwise with stirring 228 g (4.0 m) of methylisocyanate, over a period of 20 min. The reaction mixture was allowed to warm to 0° C and was maintained at this temperature for 1 hr. Then 60 g (2 m) of freshly distilled sulfur dichloride was added followed by a slow addition of 346 g (4.4 m) of pyridine at −20° to −0° C. After stirring for 2 hrs. at −10° C and for 16 hrs. at ambient temperature, the reaction mixture was diluted with 500 ml of water. The toluene layer was further washed with (3 × 500 ml) water dried and distilled to yield 244 g (66 percent) of the product. B. P. 55°–57° C/0.25 mm. m.p. 40°–41° C.

Calc'd for $C_4H_6F_2N_2O_2S$: C, 26.09; H, 3,28; N, 15.21; Found: C, 26.19; H, 3.20; N, 14.79.

EXAMPLE II

Preparation of 1-Methylsulfinyl-[N-methyl-N-(N'-methyl-N'-fluorocarbonylaminosulfenyl) carbamoyloxy] acetimidate To a solution of 4.0 grams (0.033 m) of methylsulfinyl-N-hydroxyacetimidate and 6.07 grams (0.033m) of N,N'-bis-(N-methyl-N-fluorocarbonylamino) sulfide in 100 ml of toluene was added dropwise with stirring 3.34 grams (0.033 m) of triethylamine dissolved in 50 ml of toluene. After stirring overnight the solid was filtered (desired material contaminated with bis-carbamate). The filtrate was washed with water, dried and concentrated to afford 0.5 grams of the product. Total weight of purified material from both crops was 1.55 grams, m.p. 120°–125° C (decomp.).

Infra red (KBr) 5.55 (CO), 5.78 (CO)μ.

NMR (CDCl$_3$) δ 2.36 (s), 3H, CH$_3$; 2.85 (s), 3H, CH$_3$SO; 3,43 (s), 6H, CH$_3$N.

EXAMPLE III

Preparation of S-Methyl-N-[N'[N''-(1-methylsulfinylethylidiniminooxycarbonyl)-N''-methylaminosulfenyl]-N'-methylcarbamoyloxy] thioacetimidate A mixture containing 2.42 grams (0.02 m) of methylsulfinyl-N-hydroxyacetimidate, 5.5 grams (0.02 m) of S-methyl-[N-methyl-N-(N'-methyl-N'-fluorocarbonylaminosulfenyl)-carbamoyloxy]thioacetimidate, and 2.02 grams (0.02 m) of triethylamine in 100 ml of toluene was heated at 50°–60° C for 4 hours and then stirred overnight at room temperature. The solid was filtered and taken in methylene chloride. The organic solution was washed with water, dried and concentrated to a residual solid. On recrystallization from ethylacetate-methylene chloride it afforded 3.8 grams of the solid m.p. 140°–141° C.

Calc'd for $C_{10}H_{18}N_4O_5S_3$: C, 32.34; H, 4.90; N, 15.12; Found: C, 32.41; H, 4.91; N, 14.86.

EXAMPLE IV

Preparation of
S-Methyl-N-[N'-[N''-(1-methylsulfonyle-
thylidiniminooxycarbonyl)-N''-methylaminosulfenyl]-
N'-methylcarbamoyloxy]-thioacetimidate To a suspension of 5.26 grams (0.019 m) of approximately 95 percent S-methyl-[N-methyl-N-(N'-methyl-N'-fluorocarbonylaminosulfenyl)carbamoyloxy]thioacetimidate and 2.61 grams (0.019 m) of methylsulfonyl-N-hydroxyacetimidate in 100 ml of toluene was added with stirring 1.92 grams (0.019 m) of triethylamine diluted in 50 ml of toluene. After stirring for 3 hours at room temperature the solid was filtered. Recrystallization from chloroform ethyl alcohol afforded 5.0 grams of the product. m.p. 120°–123° C.

Calc'd for $C_{10}H_{18}N_4O_6S_3$: C, 31.08; H, 4.69; N, 14.50; Found: C, 30.95; H, 4.79; N, 14.22.

EXAMPLE V

Preparation of
1-Methyl-N-[N'-[N''-(1-methylsulfinyle-
thylidiniminooxycarbonyl)-N''-methylaminosulfenyl]-
N'-methylcarbamoyloxy]-sulfinylacetimidate (METHOD III)

To a solution of 8.0 grams (0.07 m) of methylsulfinyl-N-hydroxyacetimidate and 6.45 grams (0.035 m) of N, N'-bis-(N-methyl-N-fluorocarbonylamino)sulfide in 100 ml of toluene was added dropwise 7.08 grams (0.07 m) of triethylamine. After about 15 minutes a white solid started precipitating. After stirring at room temperature for 18 hours, the solid was filtered, taken in methylene chloride. The organic solution was washed with water, dried and concentrated to a residual solid. On recrystallization from methylene chloride toluene it afforded 5.4 grams of a white solid. m.p. 131°–134° C.

Calc'd for $C_{10}H_{18}N_4O_6S_3$: C, 31.08; H, 4.69; N, 14.50; Found: C, 31.35; H, 4.54; N, 13.94.

(METHOD IV)

To a solution of 5.0 grams (0.014 m) of S-methyl-N-[N'-[N''-(1-methylthioethylidiniminooxycarbonyl)-N''-methylaminosulfenyl]-N'-methylcarbamoyloxy]-thioacetimidate in 75 ml of ethylacetate was added 12.46 grams of 25.6 percent solution of peracetic acid in ethylacetate. After stirring for 16 hours at room temperature the solid was filtered to afford 7.0 grams of the product. The melting point and spectral data was identical to the product obtained by Method I.

EXAMPLE VI

Preparation of
1-Methylsulfonyl-N-[N'-[N''-(1-methylsulfonyle-
thylidiniminooxycarbonyl)-N''-methylaminosulfenyl]-
N'-methylcarbamoyloxy]-acetimidate To a solution of 5.0 grams (0.0365 m) of methylsulfonyl-N-hydroxyacetimidate and 6.72 grams (0.0365 m) of N, N'-bis-(N-methyl-N-fluorocarbonylamino)sulfide in 150 ml of toluene was added 3.69 grams (0.0365 m) of triethylamine. After stirring for 16 hours, the solid was collected by filtration to afford after crystallization 1.1 grams of a white solid m.p. 173°–175° C (decomp.). The filtrate was predominantly the monoadduct S-methyl-[N-methyl-N-(N'-methyl-N'-fluorocarbonylaminosulfenyl)carbamoyloxy]-sulfonylacetimidate.

Calc'd for $C_{10}H_{18}N_4O_8S_3$: C, 28.70; H, 4.33; N, 13.39; Found: C, 28.64; H, 4.31; N, 13.29.

The following compounds are representative of other compounds that are within the scope of this invention that can be prepared according to this invention by selecting appropriate starting materials for use in the procedure described herein above:

1-Isopropylsulfinyl-[N-methyl-N-(N'-methyl-N'-fluorocarbonylaminosulfenyl)carbamoyloxy] acetimidate;
1-Pentylsulfonyl-[N-methyl-N-(N'-methyl-N'-fluorocarbonylaminosulfenyl)carbamoyloxy] acetimidate;
S-Isopropyl-N-[N'-[N''-(1-methylsulfinyle-thylidiniminooxycarbonyl)-N''-methylaminosulfinyl]-N'-methylcarbamoyloxy] thioacetimidate;
S-Isopropyl-N-[N'-[N''-(1-isopropylsulfinyle-thylidiniminooxycarbonyl)-N''-methylaminosulfenyl]-N'-methylcarbamoyloxy] thioacetimidate;
S-Isopropyl-N-[N'-[N''-(1-isopropylsulfonyle-thylidiniminooxycarbonyl)-N'-methylaminosulfenyl]-N'-methylcarbamoyloxy] thioacetimidate;
1-Isopropylsulfonyl-[N-methyl-N-(N'-methyl-N'-fluorocarbonylaminosulfenyl)carbamoyloxy] acetimidate;
1-Butylsulfinyl-[N-methyl-N-(N'-methyl-N'-fluorocarbonylaminosulfenyl)carbamoyloxy] acetimidate.

Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of test compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis Fabae Scop.*) reared on potted dwarf nasturtium plants at 65°–70° F and 50–70 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being uprighted were considered dead. Aphids remaining on the plants were observed closely for movement and those which were unable to move the length of the body upon stimulator by prodding were considered dead. Percent mortality was recorded for various concentration levels.

Southern Armyworm Leaf Spray Test

Larvae of the southern armyworm (*Prodenia Eridania*, (Cram.), reared on Tendergreen bean plants at a temperature of 80±5° F. and relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig. air pressure.

This application which lasted 25 seconds was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for 3 days. Although the larvae could easily consume the whole leaf within 24 hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis, Muls.*) reared on Tendergreen bean plants at a temperature of 80±5° and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F. for 3 days. Although the larvae could easily consume the leaf within 24 to 48 hours, no more food was added. Larvae which were unable to move the length of the body, even upon stimulation, were considered dead.

Fly Bait Test

Four to 6 day old adult house flies (*Musca domestica, L.*) reared according to the specifications of the Chemical Specialties Manufacturing Association (Blue Book, McNair-Dorland Co., NY., 1954; pages 243-244, 261) under controlled conditions of 80±5° F. and 50±5 percent relative hmidity, were the test insects. The flies were immobilized by anesthetizing with carbon dioxide and 25 immobilized individuals, males and females, were transferred to a cage consisting of a standard food strainer about 5 inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one inch square of an absorbent cotton pad. This bait cup was introduced and centered on the blotting paper under the food strainer prior to admitting the anesthetized flies. The caged flies were allowed to feed on the bait for 24 hours, at a temperature of 80±5° F. and the relative humidity of 50±5 percent. Flies which showed no sign of movement on prodding were considered dead.

Mite Foliage Spray Test

Adults and nymphal stages of the two-spotted mite (*Tetranychus urticae Koch*), reared on Tendergreen bean plants at 80±5 percent relative humidity, were the test organisms. Infested leaves from a stock culture were placed on the primary leaves of two bean plants 6 to 8 inches in height, growing in a 2½ inch clay pot. 150-200 Mites, a sufficient number for testing, transferred from the excised leaves to the fresh plants in a period of 24 hours. Following the 24 hour transfer period, the excised leaves were removed from the infested plants. The test compounds were formulated by diluting the stock suspension with water to give a suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted for 25 seconds was sufficient to wet the plants to run-off. As a control, 100-110 milliliters of a water solution containing acetone and emulsifier in the same concnetrations as the test compound formulation, but containing no test compound, were also sprayed on infested plants. The sprayed plants were held at 80±5 percent relative humidity for 6 days, after which a mortality count of motile forms was made. Microscopic examination for motile forms was made on the leaves of the test plants. Any individual which was capable of locomotion upon prodding, was considered living.

The results of these tests are set forth in Table I below. In these tests the pesticidal activity of the compounds against aphid, mite, Southern Armyworm, Mexican Bean Beetle, and house fly was rated as follows:
A = Excellent control
B = Partial control
C = No control

Mammalian Toxicity Test

Certain of these compositions were also evaluated to determine their peroral toxicity to mammals. The animal selected for this experiment was the rat. The test results obtained are expressed in terms of the number of milligrams of compositions per kilogram of weight of the animal required to achieve a morality rate of 50 percent ($LD_{50}$).

The results of all of these tests are set forth in Table I below:

be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable

TABLE I

| Structure | BIOLOICAL DATA | | | | | |
|---|---|---|---|---|---|---|
| | Aphid | Mite | Southern Armyworm | Mexican Bean Beetle | Housefly | A. O. Rat |
| CH₃—C(=NOC)(SCH₃)—N(CH₃)—S—N(CH₃)—C(=O)—O—N=C(CH₃)—S(=O)CH₃ | A | C | A | A | A | 202 |
| CH₃—C(=NOC)(SCH₃)—N(CH₃)—S—N(CH₃)—C(=O)—O—N=C(CH₃)—S(=O)(=O)CH₃ | A | A | A | A | A | 285 |
| (CH₃—C(=NOC)—N(CH₃)(S=O,CH₃))₂S | C | C | C | C | A | — |
| (CH₃—C(=NOC)—N(CH₃)(O=S=O,CH₃))₂S | C | C | C | C | A | — |

The data in TABLE I clearly illustrates the broad spectrum high level pesticidal activity exhibited by the compounds of this invention. It should be understood that the pests evaluated are representative of a wider variety of pest which can be controlled by the compounds of this invention.

The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre.

The pesticides contemplated herein prevent attack by insects, nematodes and mites upon plants or other mate-

What is claimed is:

1. A compound of the formula:

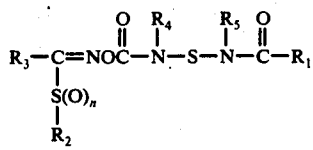

wherein:

n is 1 or 2;

R₁ is fluorine or

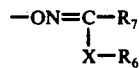

X is sulfur, sulfinyl or sulfonyl;

R₂, R₃, R₄, R₅, R₆ and R₇ are individually alkyl having from 1 to 8 carbon atoms.

2. A compound according to claim 1 wherein R₂, R₃, R₄, R₅, R₆ and R₇ are individually alkyl having from 1 to 5 carbon atoms.

3. A compound according to claim 1 wherein R₄ and R₅ are methyl.

4. A compound according to claim 1 wherein R₃ and R₇ are methyl.

5. A compound according to claim 1 wherein R₁ is fluorine.

6. A compound according to claim 1 wherein R₁ is

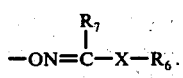

7. 1-methylsulfinyl-[N-methyl-N-(N'-methyl-N'-fluorocarbonylaminosulfenyl)carbamoyloxy] acetimidate.

8. S-methyl-N-[[N'-[N''-(1-methylsulfinylethylidiniminooxycarbonyl)-N''-methylaminosulfenyl]-N'-methylcarbamoyloxy]]thio acetimidate.

9. S-methyl-N-[[N'-[N''-(1-methylsulfonylethylidiniminooxycarbonyl)-N''-methylaminosulfenyl]-N'-methylcarbamoyloxy]]thioacetimidate.

10. An insecticidally, nematocidally and miticidally active composition comprising an acceptable carrier and an insecticidally, nematocidally or miticidally effective amount of a compound of the formula:

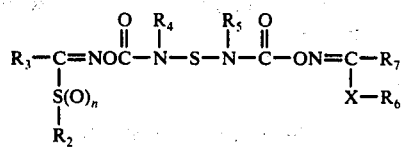

wherein:

n is 1 or 2;

X is sulfur, sulfinyl or sulfonyl;

R₂, R₃, Rhd 4, R₅, R₆ and R₇ are individually alkyl having from 1 to 8 carbon atoms.

11. A composition according to claim 10 wherein R₂, R₃, R₄, R₅, R₆ and R₇ are individually alkyl having from 1 to 5 carbon atoms.

12. A composition according to claim 10 wherein R₄ and R₅ are methyl.

13. A composition according to claim 10 wherein R₃ and R₇ are methyl.

14. A composition according to claim 10 wherein the active toxicant is S-methyl-N-[[N'-[N''-(1-methylsulfinylethylidiniminooxycarbonyl)-N''-methylaminosulfenyl)-N'-methylcarbamoyloxy]]thioacetimidate.

15. A composition according to claim 10 wherein the active toxicant is S-methyl-N-[[N'-[N''-(1-methylsulfonylethylidiniminooxycarbonyl)-N''-methylaminosulfenyl]-N'-methylcarbamoyloxy]]thiocetimidate.

16. A method of controlling insects, mites and nematodes which comprises subjecting them to an insecticidally nematocidally or miticidally effective amount of a compound of the formula:

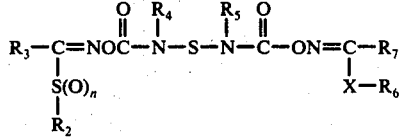

wherein:

n is 1 or 2;

X is sulfur, sulfinyl or sulfonyl;

R₂, R₃, R₄, R₅, R₆ and R₇ are individually alkyl having from 1 to 8 carbon atoms.

17. A method according to claim 16 wherein R₂, R₃, R₄, R₅, R₆ and R₇ are individually alkyl having from 1 to 5 carbon atoms.

18. A method according to claim 16 wherein R₄ and R₅ are methyl.

19. A method according to claim 16 wherein R₃ and R₇ are methyl.

20. A method according to claim 16 wherein the compound is S-methyl-N-[[N'-[N''-(1-methylsulfinylethylidiniminooxycarbonyl)-N''-methylaminosulfenyl-N'-methylcarbamoyl]-oxy]]thiocetimidate.

21. A method according to claim 16 wherein the compound is S-methyl-N-[[N'-[N''-(1-methylsulfonylethylidimiminooxycarbonyl)-N''-methylaminosulfenyl]-N'-methylcarbamoyloxy]]thioacetimidate.

UNITED STATES PATENT OFFICE
CERTIFICATE OF CORRECTION

Patent No. 4,072,751  Dated February 7, 1978

Inventor(s) Themistocles D.J. D'Silva

It is certified that error appears in the above-identified patent and that said Letters Patent are hereby corrected as shown below:

Column 2, line 60 which reads -- flouride -- should read "fluoride".

Column 9 and 10, the heading of Table I which reads, -- BIOLOICAL -- should read, "BIOLOGICAL".

Column 9, the last compound in Table I which reads,

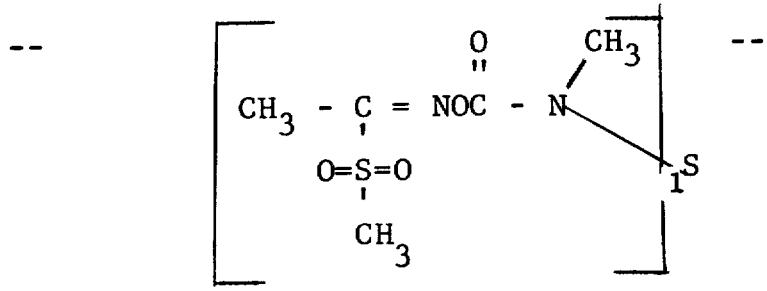

UNITED STATES PATENT OFFICE
CERTIFICATE OF CORRECTION

Patent No. 4,072,751　　　　Dated February 7, 1978

Inventor(s) Themistocles D.J. D'Silva

It is certified that error appears in the above-identified patent and that said Letters Patent are hereby corrected as shown below:

should read

" 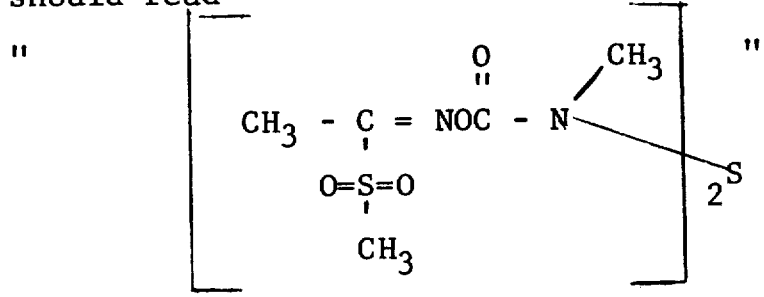 "

Column 12, line 19, which reads -- $R_2$, $R_3$, $Rhd_4$, $R_5$, $R_6$, $R_7$ -- should read "$R_2$, $R_3$, $R_4$, $R_5$, $R_6$ and $R_7$".

Column 12, lines 34 and 62 which read -- Thiocetimidate -- should read "Thioacetimidate".

UNITED STATES PATENT AND TRADEMARK OFFICE
CERTIFICATE OF CORRECTION

PATENT NO. : 4,072,751

DATED : February 7, 1978

INVENTOR(S) : Themistocles D. J. D'Silva

It is certified that error appears in the above-identified patent and that said Letters Patent are hereby corrected as shown below:

Column 3, lines 38 and 39, "oxidising" should read -- oxidizing --.

Column 4, line 37, "H,3,28" should read -- H, 3.28 --.

Column 4, line 59, "3,43"should read -- 3.43 --.

Column 8, line 56, "suspension with water to give a suspension with water" should read -- suspension with water --.

Signed and Sealed this

Seventeenth Day of April 1979

[SEAL]

Attest:

RUTH C. MASON
Attesting Officer

DONALD W. BANNER
Commissioner of Patents and Trademarks